US00PP32031P3

(12) United States Plant Patent
Pierron-Darbonne

(10) Patent No.: US PP32,031 P3
(45) Date of Patent: Aug. 4, 2020

(54) RASPBERRY PLANT NAMED 'PLAPINK 1004'

(50) Latin Name: ***Rubus idaeus* L.**
Varietal Denomination: Plapink 1004

(71) Applicant: Plantas de Navarra, S.A. Sociedad Unipersonal, Valtierra (ES)

(72) Inventor: Alexandre Pierron-Darbonne, Pamplona (ES)

(73) Assignee: Plantas de Navarra, S.A. Sociedad Unipersonal, Valtierra, Navarra (ES)

( * ) Notice: Subject to any disclaimer, the term of this patent is extended or adjusted under 35 U.S.C. 154(b) by 0 days.

(21) Appl. No.: 16/501,074

(22) Filed: Feb. 19, 2019

(65) Prior Publication Data

US 2020/0053927 P1 Feb. 13, 2020

(30) Foreign Application Priority Data

Aug. 10, 2018 (QZ) ..... PBR 2018/2081

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 6/7499
See application file for complete search history.

*Primary Examiner* — Anne Marie Grunberg
(74) *Attorney, Agent, or Firm* — Knobbe, Martens, Olson & Bear, LLP

(57) ABSTRACT

Described herein is a new and distinct variety of raspberry plant with varietal denomination 'Plapink 1004', characterized by a combination of traits which include, but are not limited to, a medium spines density and very abundant production of light red colored, conical shaped, and medium fruit size. 'Plapink 1004' is a self-fertile variety.

17 Drawing Sheets

Botanical classification: *Rubus idaeus* L.

Variety denomination: The new plant has the varietal denomination 'Plapink 1004'.

CROSS-REFERENCE TO RELATED APPLICATIONS

This application claims the benefit of European Community Plant Variety Office Application No. 2018/2081, for a raspberry variety named 'Plapink 1004', filed on Aug. 10, 2018, the entirety of which is incorporated by reference herein.

BACKGROUND

Disclosed herein is a new and distinct raspberry variety. The varietal denomination of the new variety is 'Plapink 1004'. The new variety was designated by the breeder as '10.09R.04'. The new variety of raspberry was created in a breeding program by crossing two parents; in particular, by crossing as seed parent an undistributed raspberry parent designated '0750' (unpatented) and as pollen parent an undistributed raspberry parent designated '0919' (unpatented). Female and male are selections from Applicant's breeder's program. Both parental varieties have not been commercialized.

The resulting seedling of the new variety was grown and asexually propagated by root cuttings in Segovia, Spain, 3° 59'W., 41° 22'N., 2742 feet elevation. Clones of the new variety were further asexually propagated and extensively tested. This propagation and testing has demonstrated that the combination of traits disclosed herein which characterize the new variety are fixed and retained true to type through successive generations of asexual reproduction.

The growing period in Huelva, Spain, where the observations on primocane production were made, is between about June 15 and May 15 of the following year.

SUMMARY

The present invention relates to a new and distinct raspberry variety. The varietal denomination of the new variety is 'Plapink 1004', that produces and maintains a strong vigorous plant with consistent fruit production from the end of September through the beginning of December on primocanes and in the ensuing year middle in February and middle in May.

Among the characteristics which appear to distinguish the new variety from other varieties are a combination of traits which include a medium spine density and very abundant production of light red colored (RHS red group color near 41 A to 42 A), conical shaped, and medium fruit size.

COMPARISON TO THE PARENTS

Neither the seed parental cultivar, '0750', nor the pollen parent cultivar, '0919', has any patent or application for Plant Patent Rights in any country in the world.

Both the seed and pollen parentals are selections from the Applicant's breeder's program. The Applicant maintains them in their nurseries, and both parental cultivars have never been commercialized.

The new variety is distinguished therefrom its parents by the following characteristics possessed by 'Plapink 1004' which are different than, or not possessed by, the seed parent designated '0750' (unpatented) and the pollen parent designated '0919' (unpatented).

Stipules in the leaf of seed parent '0750' (unpatented) longer than in the leaf of 'Plapink 1004'.

Seed parent '0750' (unpatented) shows a wider terminal leaflet than 'Plapink 1004'.

Seed parent '0750' (unpatented) and pollen parent '0919' (unpatented) show a leaf with relative position of lateral leaflets overlapping, whereas the position of the lateral leaflets in the new variety 'Plapink 1004' is free.

Pollen parent '0919' (unpatented) shows a green color of underside of leaf lighter than the new variety 'Plapink 1004', which has a greyed-green leaf underside color (RHS greyed-green group near 191C to 191 B).

In pollen parent '0919' (unpatented) the plug is much longer than broad and the attitude of sepals is outwards, whereas the new variety 'Plapink 1004' presents a plug moderately longer than broad and the attitude of sepals is upwards.

COMPARISON TO CLOSEST VARIETY

The new variety 'Plapink 1004' is closest to the variety 'Adelita' (patented in U.S. Plant Pat. No. 25,245), but is distinguished therefrom by the following characteristics possessed by 'Plapink 1004' which are different than, or not possessed by, 'Adelita' (U.S. Plant Pat. No. 25,245).

Leaf green color of underside in 'Adelita' (U.S. Plant Pat. No. 25,245) is a green color (RHS green group near 138 B to 136 C), whereas in 'Plapink 1004' it is a greyed-green color (RHS greyed-green group near 191C to 191 B).

'Adelita' (U.S. Plant Pat. No. 25,245) shows equally three and five leaflets by leaf, whereas 'Plapink 1004' shows three.

The relative position of lateral leaflets in the leaf of 'Adelita' (U.S. Plant Pat. No. 25,245) is overlapping, whereas the relative position of lateral leaflets in the leaf of 'Plapink 1004' is free.

Current season's cane of 'Adelita' (U.S. Plant Pat. No. 25,245) shows a yellow-green color (RHS yellow-green group near 144 D to 144 C), whereas current season's cane of 'Plapink 1004' shows a green color (RHS green group near 143 C to 143 B).

'Adelita' (U.S. Plant Pat. No. 25,245) shows a sparse spine density, and the length of spines is very short to short, whereas 'Plapink 1004' shows a medium spine density, and the length of spines is medium-to-long.

'Adelita' (U.S. Plant Pat. No. 25,245) shows a red color fruit (RHS red group near 47 A to 46 A), whereas 'Plapink 1004' shows a fruit red color fruit (RHS red group near 41 A to 42 A).

Time of beginning of flowering on currents season's cane of 'Adelita' (U.S. Plant Pat. No. 25,245) is early to medium, whereas time of beginning of flowering on currents season's cane of 'Plapink 1004' is very early.

Time of beginning of fruit ripening on current year's cane of 'Adelita' (U.S. Plant Pat. No. 25,245) is early; whereas time of beginning of fruit ripening on current year's cane of 'Plapink 1004' is very early. Differences in the leaf color underside of 'Plapink 1004' (designated '10.09R.04') and 'Adelita' (U.S. Plant Pat. No. 25,245) are show in FIG. 4 and FIG. 15.

Differences in the relative position of lateral leaflets in the leaf of 'Plapink 1004' (designated '10.09R.04') and 'Adelita' (U.S. Plant Pat. No. 25,245) are shown in FIG. 3 and FIG. 15.

Differences in the color of current season's cane of 'Plapink 1004' (designated '10.09R.04') and 'Adelita' (U.S. Plant Pat. No. 25,245) are shown in FIG. 7 and FIG. 16.

Differences in spine density and spine length of 'Plapink 1004' (designated '10.09R.04') and 'Adelita' (U.S. Plant Pat. No. 25,245) are shown in FIG. 7 and FIG. 16.

Differences in fruit color of 'Plapink 1004' (designated '10.09R.04') and 'Adelita' (U.S. Plant Pat. No. 25,245) are shown in FIG. 11, FIG. 12 and FIG. 17.

These differences are maintained during the harvest season.

BRIEF DESCRIPTION OF THE ILLUSTRATIONS

The accompanying photographs show typical specimens of the new variety, of 'Plapink 1004', designated '10.09R.04' in the illustrations, including fruit, foliage and flower, in color as nearly true as it is reasonably possible to make in color illustrations of this character.

The plants depicted in the drawings were planted June 15 in the farm of La Mogalla in Cartaya (Huelva), Spain, about 7° W, 37° N, 45 feet elevation.

Drawings were taken November (about November 2 and November 13): minimum temperate about 7° to 9° Centigrade, maximum temperate about 18 to 22° Centigrade.

FIG. 1 and FIG. 2 shows several plants of the new variety (designated 10.09R.04) which exhibit a semi-upright habit plant with several light red colored and conical shape fruits.

FIG. 3 and FIG. 4 show the upper side and the underside, respectively, of a complete leaf of the new variety (designated 10.09R.04). In it, we can see that the leaf color of the upper side of the new variety (designated 10.09R.04) is a green color (RHS green group near 138 B to 138 A) and the leaf color of underside of the new variety (designated 10.09R.04) is a greyed-green color (RHS greyed-green group near 191C to 191 B). It can be see that relative position of lateral leaflets in the leaf of the new variety (designated 10.09R.04) is free.

FIG. 5 and FIG. 6 show the upper side and the underside, respectively, of the terminal leaflet of the new variety (designated 10.09R.04). In it, we can see that the terminal leaflet color of upper side of the new variety (designated 10.09R.04) is a green color (RHS green group near 138 B to 138 A) and the terminal leaflet color of underside of the new variety (designated 10.09R.04) is a greyed-green color (RHS greyed-green group near 191C to 191 B).

Figure 1:
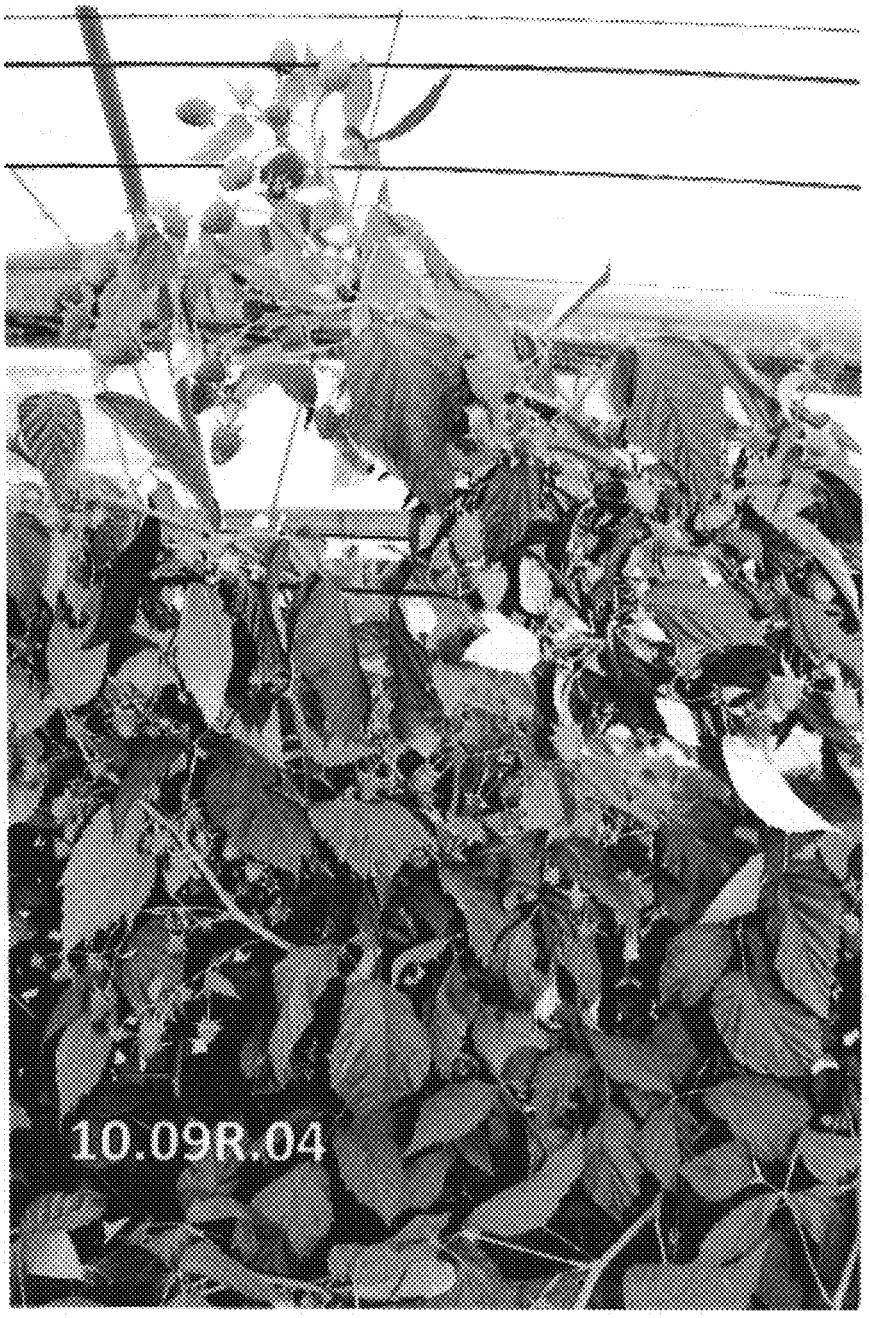
Figure 2:
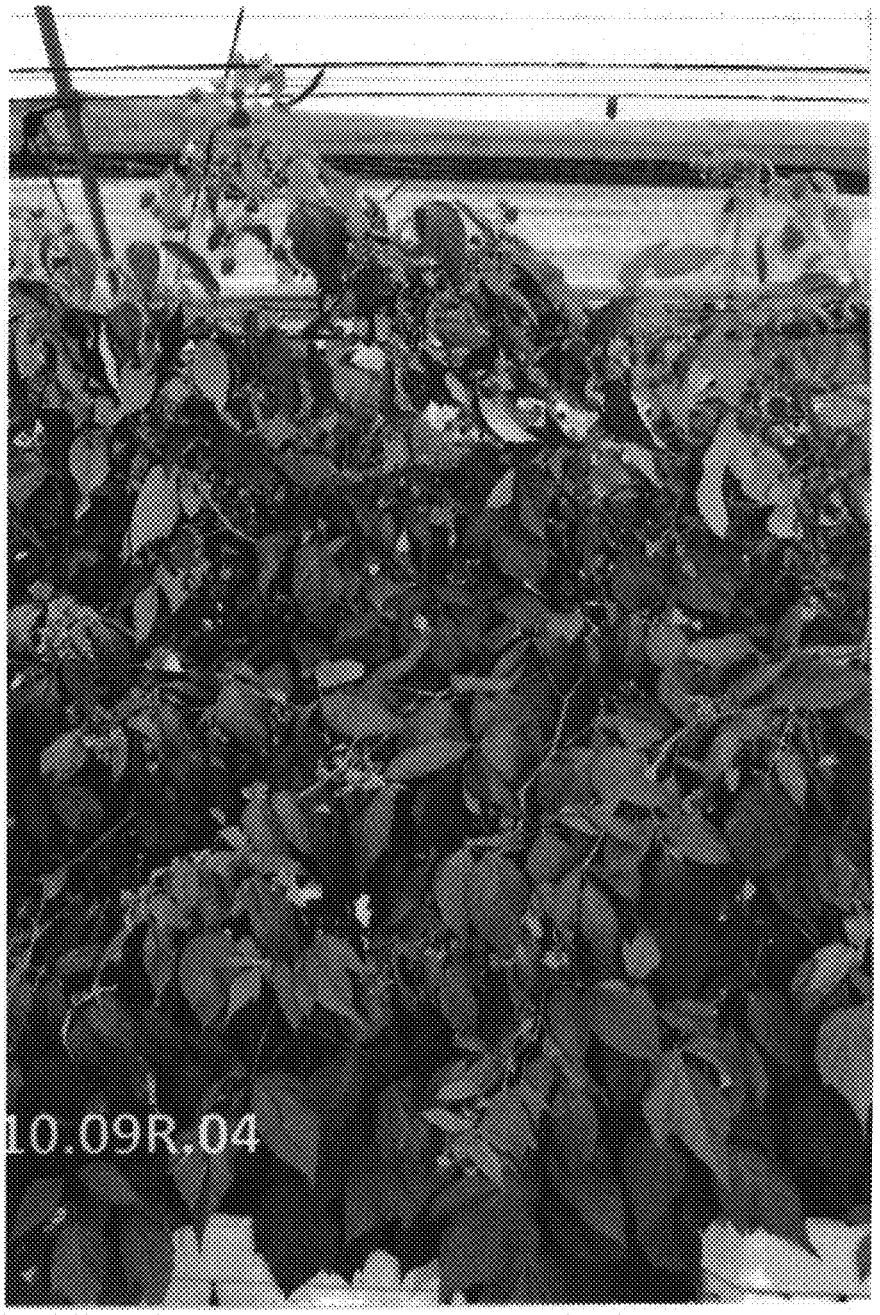
Figure 3:
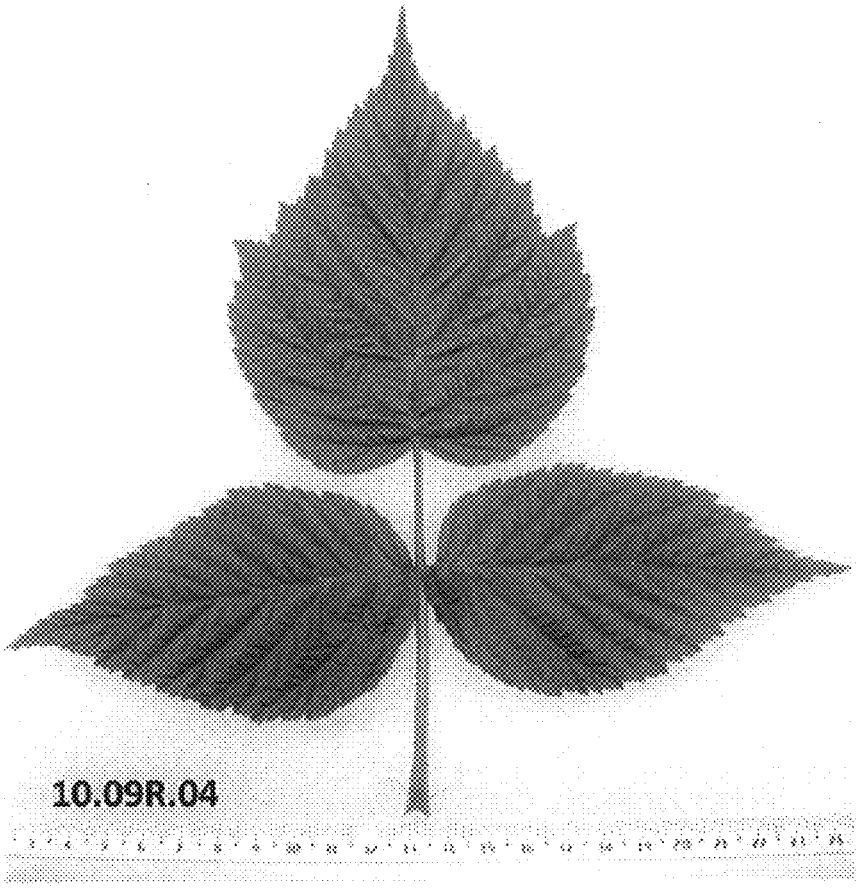
Figure 4:
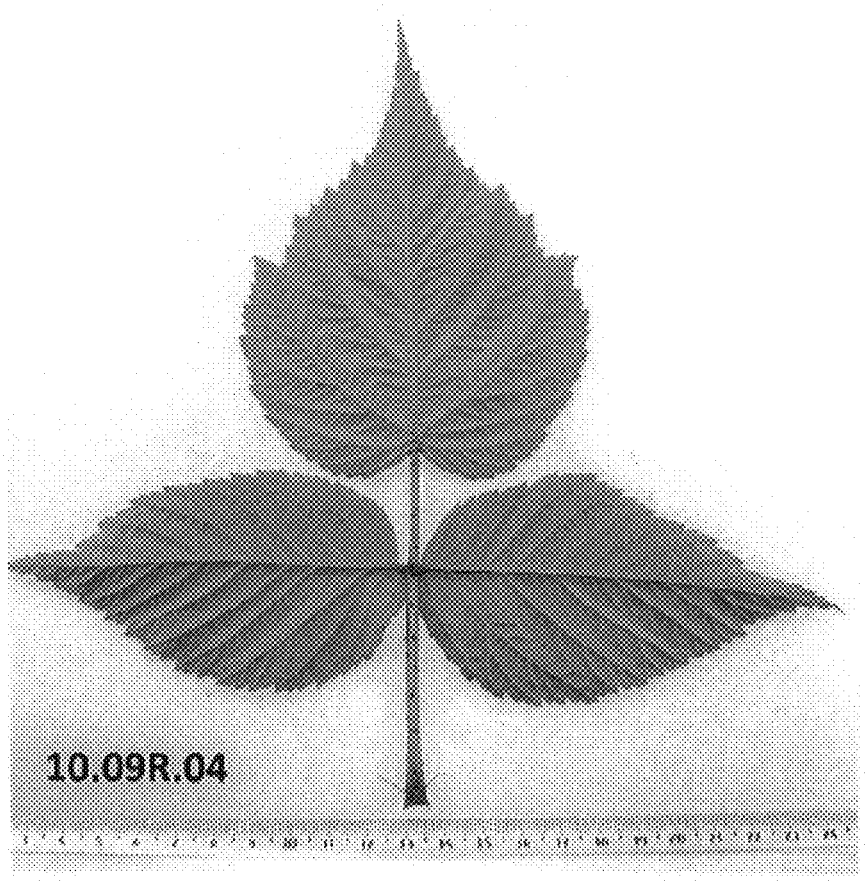
Figure 5:
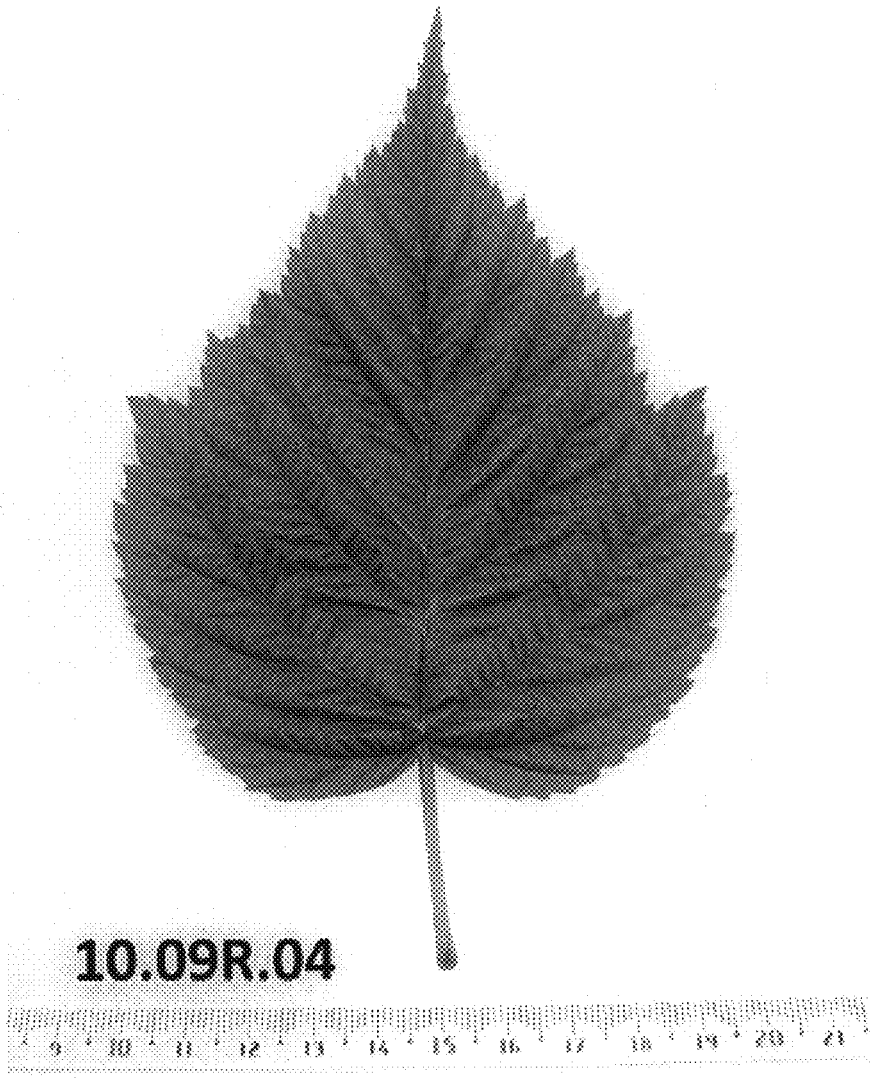
Figure 6:
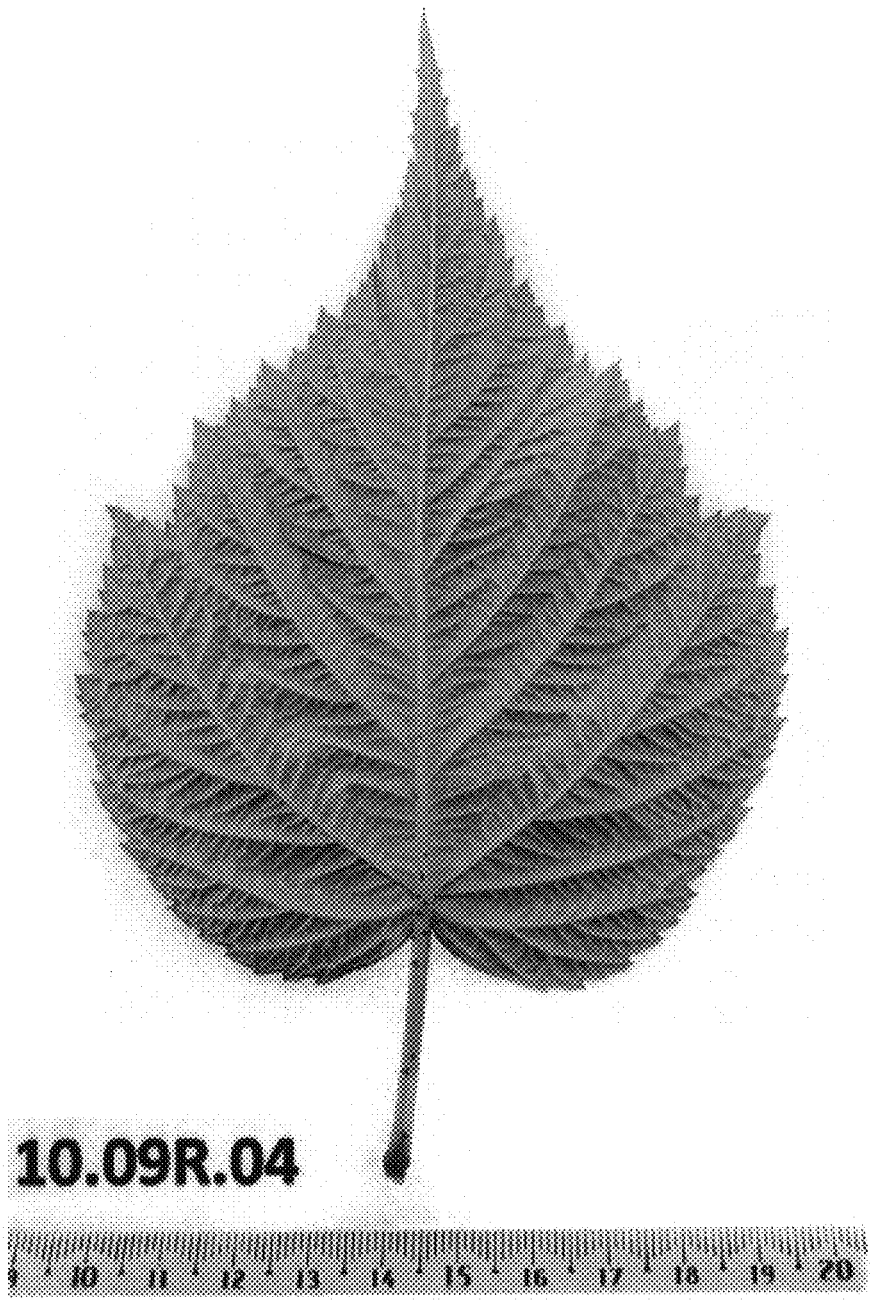
Figure 7:
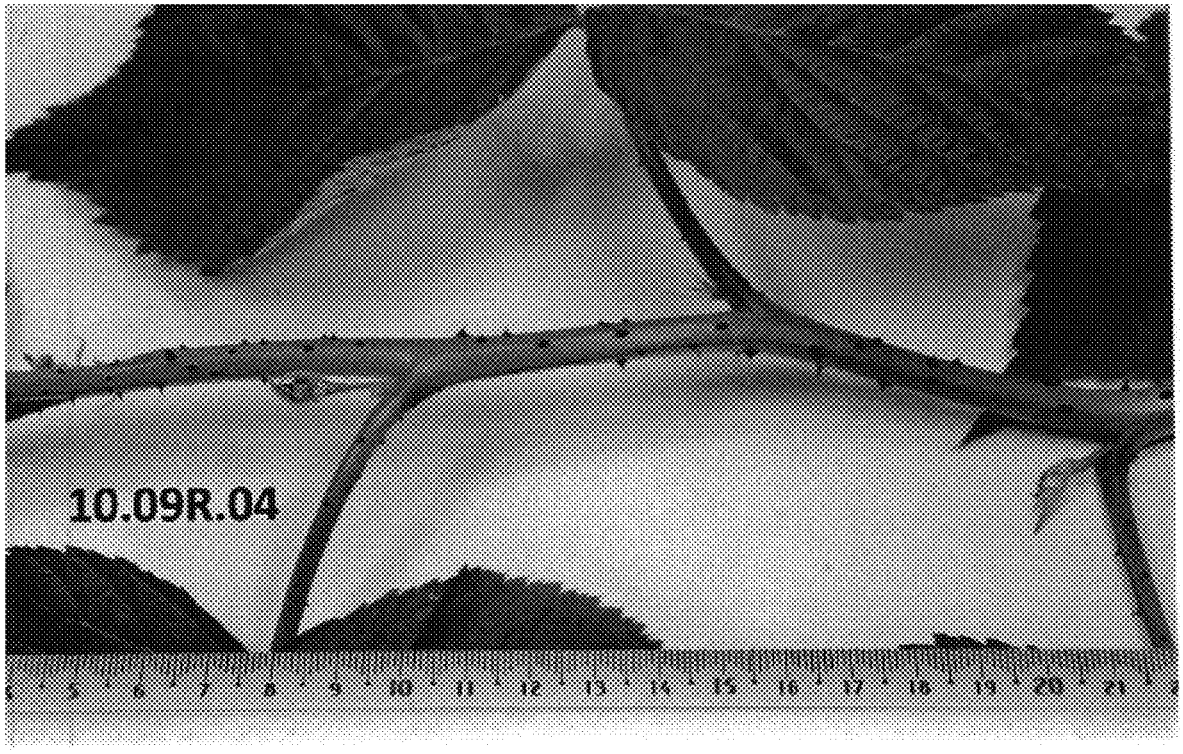
FIG. 7 shows the current season's cane of the new variety (designated 10.09R.04) with a green color (RHS green group near 143 C to 143 B), sparse spine density and spine length of very short to short.
Figure 8:
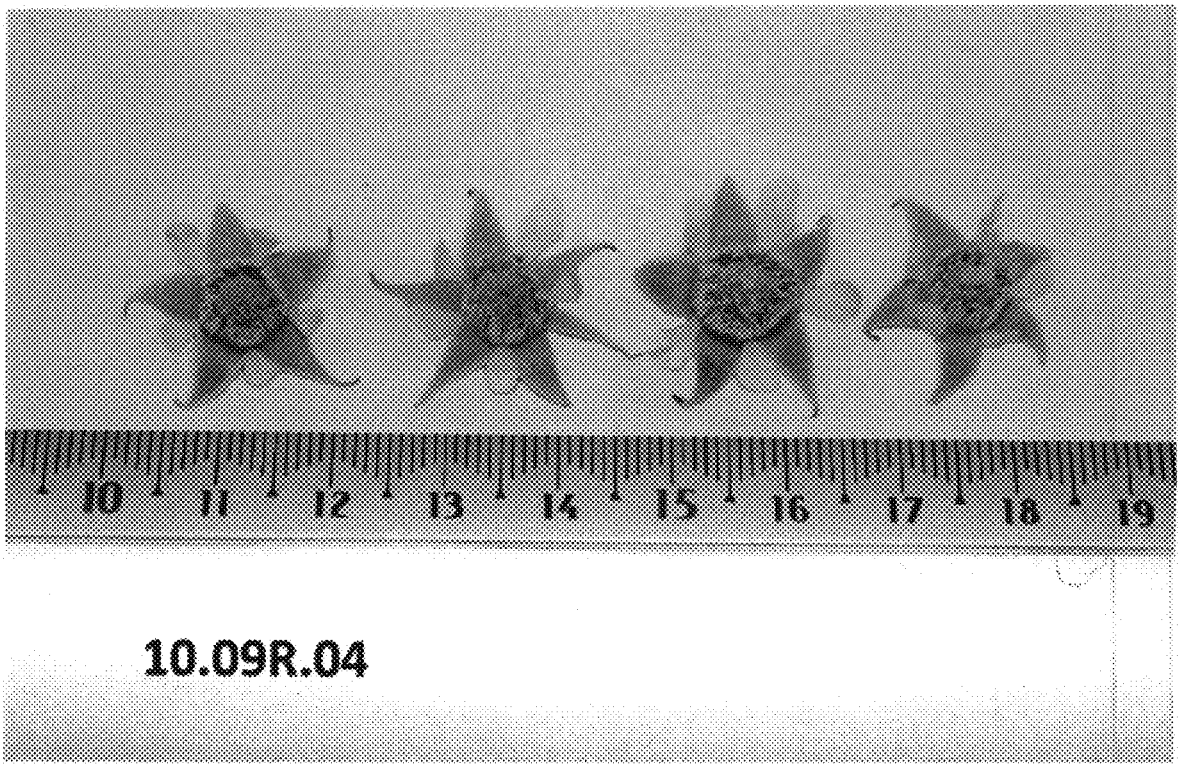
FIG. 8 shows typical flowers of the new variety (designated 10.09R.04).
Figure 9:
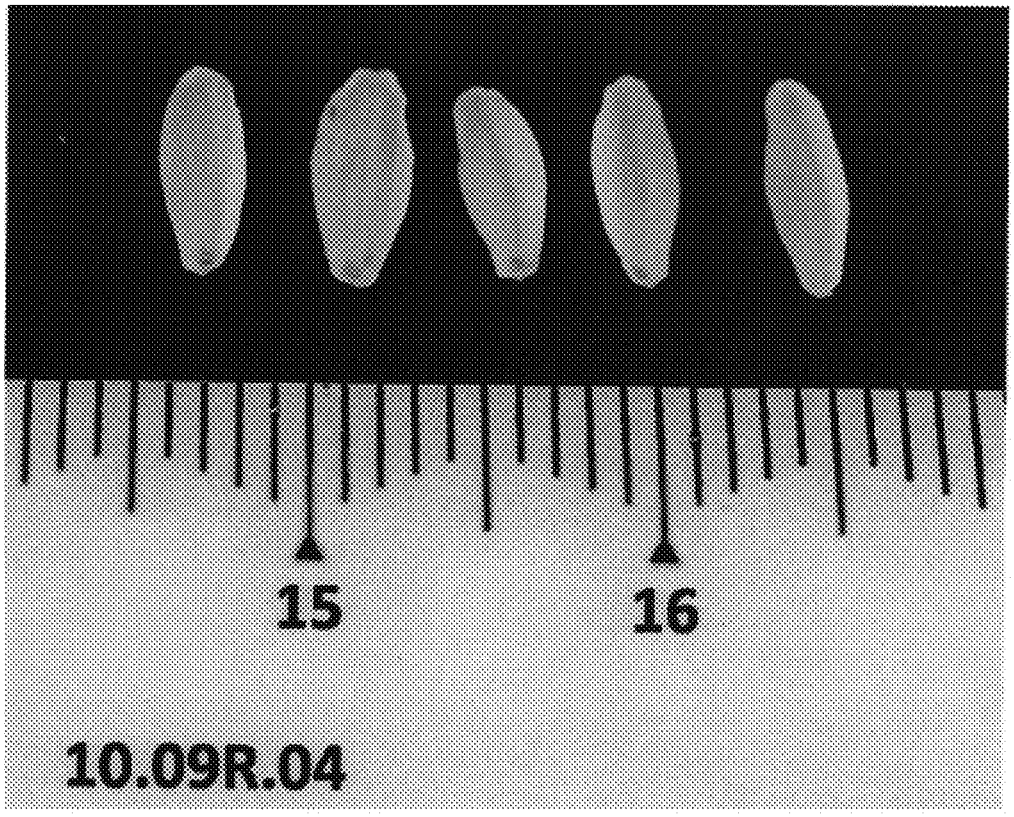
FIG. 9 shows typical petals of the new variety (designated 10.09R.04) with narrow elliptique shape and RHS white group color (near 155 D).
Figure 10:
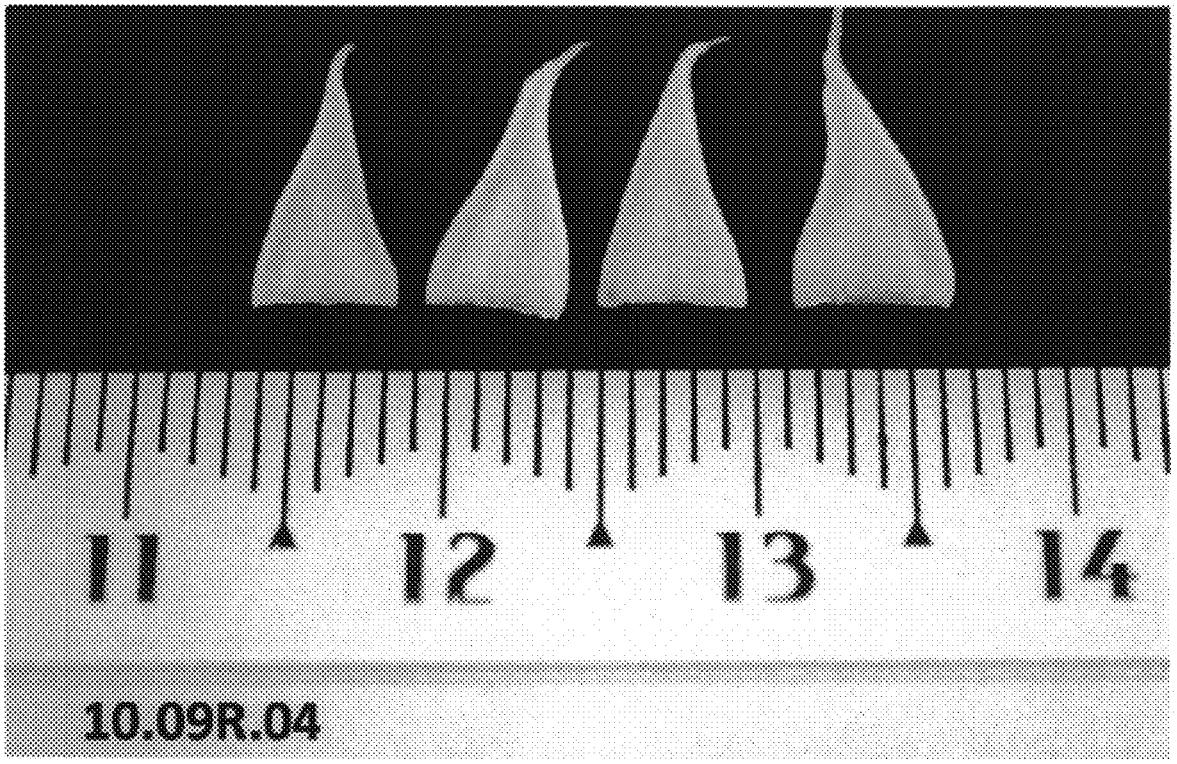
FIG. 10 shows typical sepals of the new variety (designated 10.09R.04) with triangular shape, acuminate apex and RHS yellow-green group color (near 145 C to 145 B).
Figure 11:
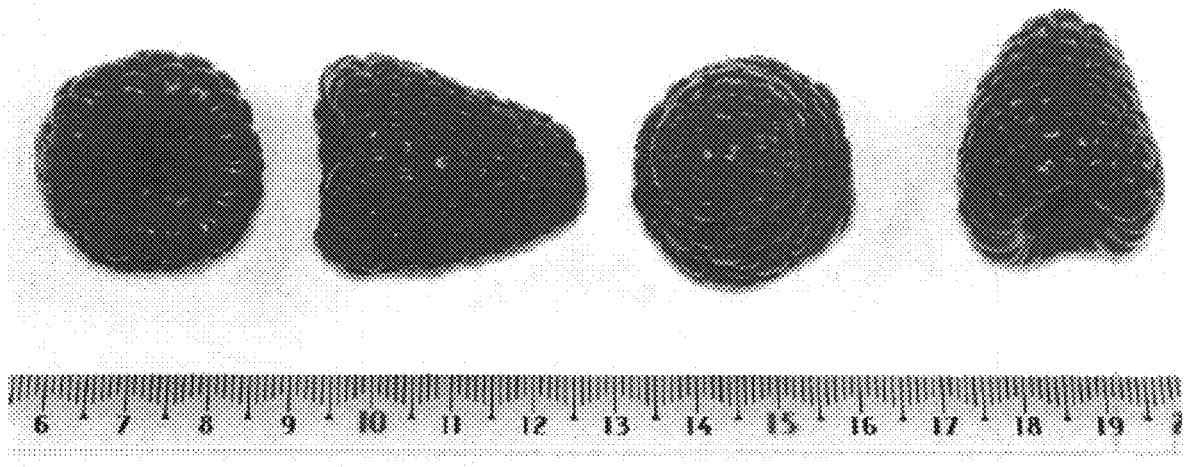
FIG. 11 and FIG. 12 show typical fruits of the new variety (designated 10.09R.04) with conical shape in lateral view, and red color (RHS red group near 41 A to 42 A).
Figure 12:
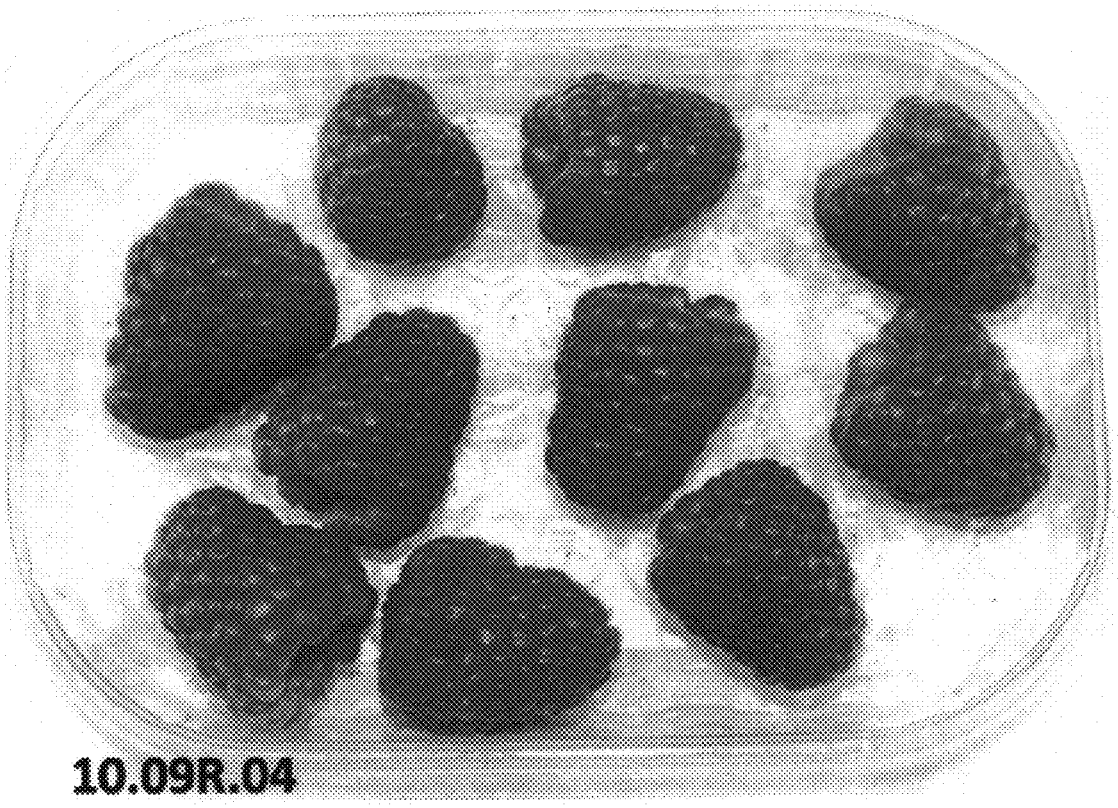
Figure 13:
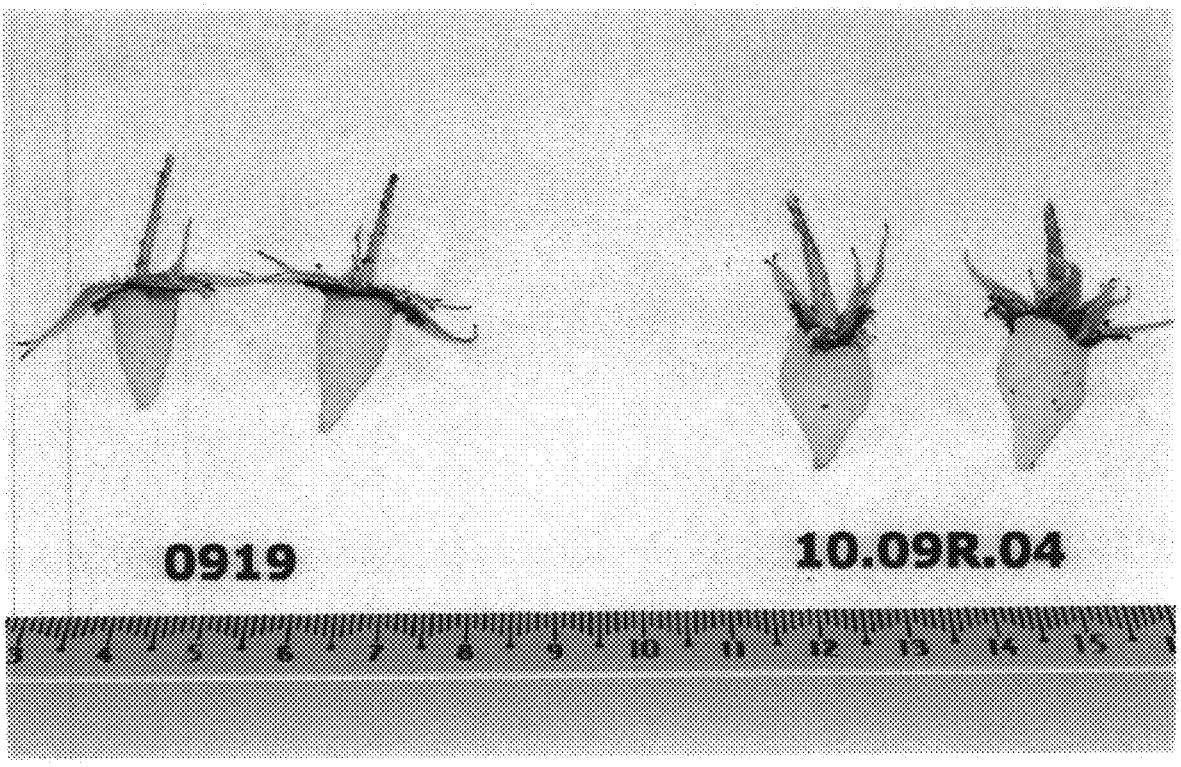
FIG. 13 shows typical receptacles of the new variety (designated 10.09R.40) with conical shape, moderately longer than broad, attitude of sepals upwards and yellow-white color (RHS yellow-white group near 158 B to 158 A) in comparison with their pollen parent '0919' (unpatented), which shows a plug much longer than broad and an outwards attitude of sepals.
Figure 14:
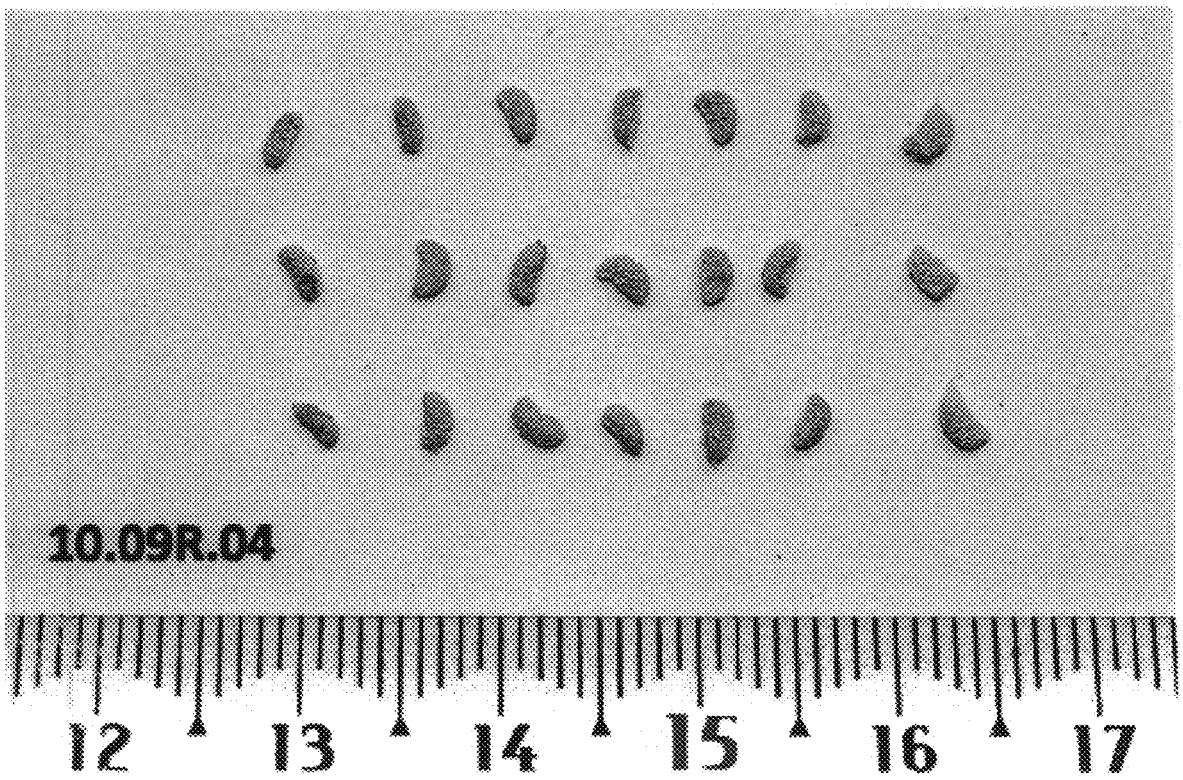
FIG. 14 shows typical seeds of the new variety (designated 10.09R.04) with slightly reniform shape, greyed-orange color (RHS greyed-orange group near 165 C to 164 B) and wrinkled surface texture.
Figure 15:
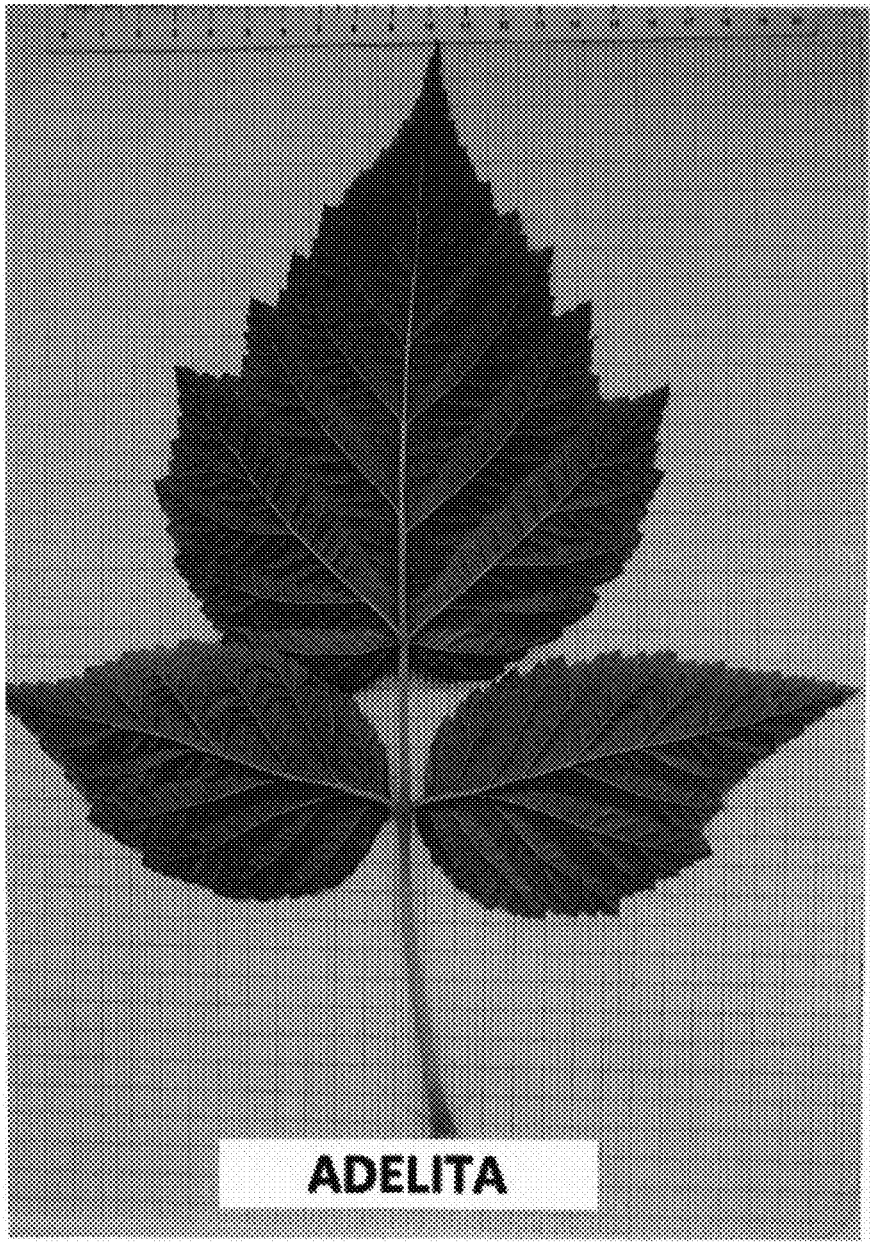

FIG. 15 shows the underside of a complete leaf of the raspberry variety 'Adelita' (U.S. Plant Pat. No. 25,245). In it we can see that leaf color of underside of raspberry variety 'Adelita' (U.S. Plant Pat. No. 25,245) is a green color (RHS green group near 138 B to 136 C) and the relative position of lateral leaflets in the leaf of 'Adelita' (U.S. Plant Pat. No. 25,245) is overlapping.

Figure 16:
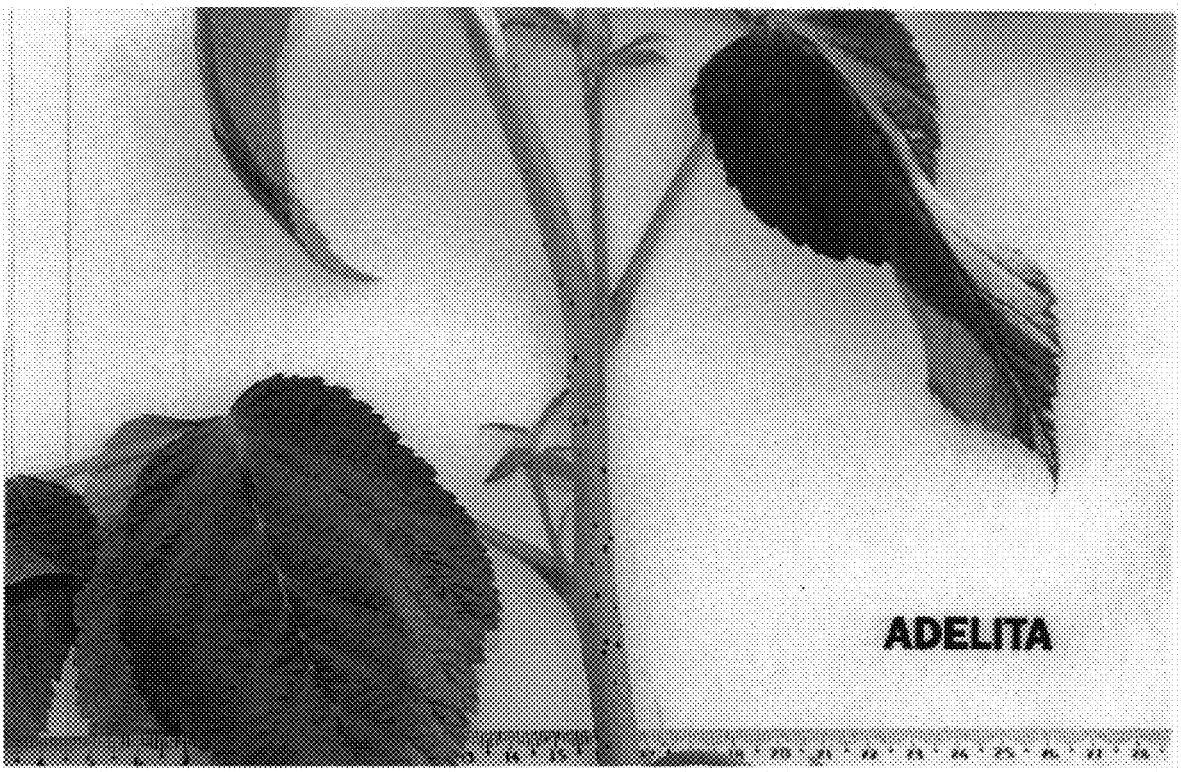

FIG. 16 shows the current season's cane of 'Adelita' (U.S. Plant Pat. No. 25,245) with a yellow- green color (RHS yellow-green group near 144 D to 144 C), with sparse spines density and very short to short spine length.

Figure 17:
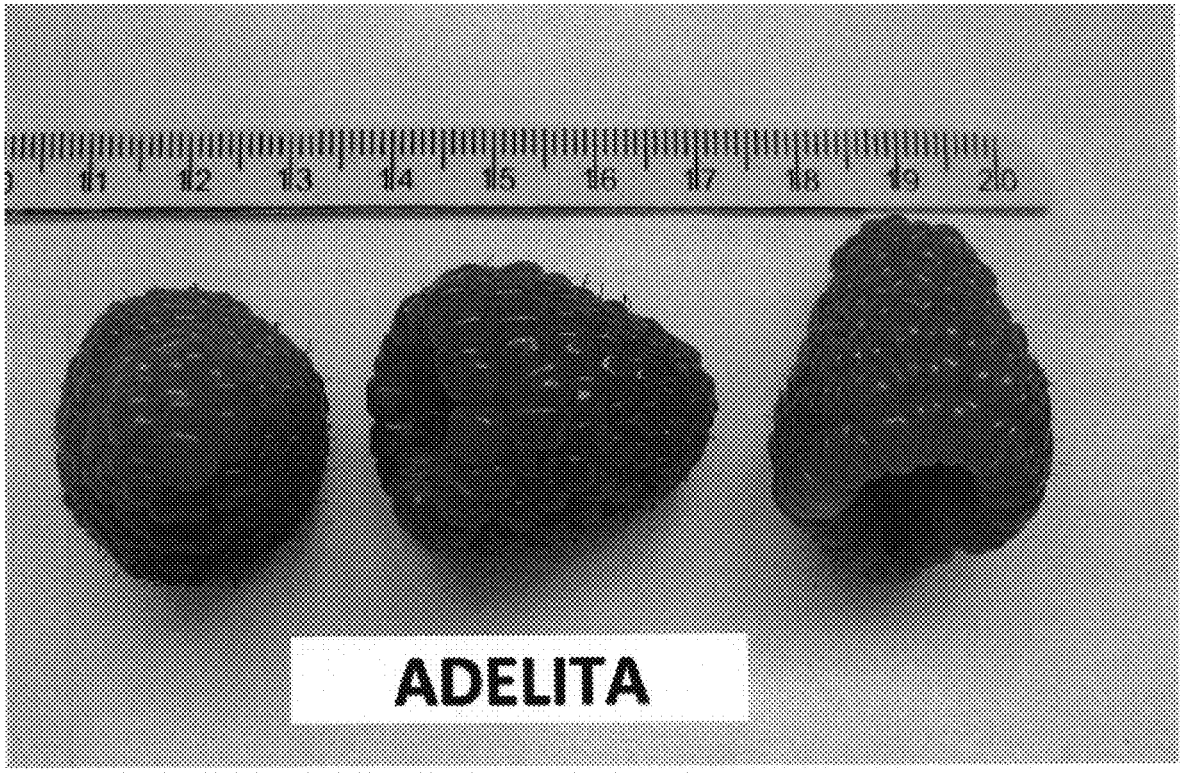

FIG. 17 shows the fruit of raspberry variety 'Adelita' (U.S. Plant Pat. No. 25,245), which shows a red color fruit (RHS red group near 47 A to 46 A).

DESCRIPTION OF THE NEW VARIETY

The following description is in accordance with UPOV terminology and the color terminology herein is in accordance with The Royal Horticultural Society Colour Chart (R.H.S.C.C.), 3rd edition published in 1995.

The color descriptions and other phenotypical descriptions may deviate from the stated values and descriptions depending upon variation in environmental, seasonal, climatic and cultural conditions.

Throughout this specification, color names beginning with a small letter signify that the name of that color, as used in common speech is aptly descriptive. Color names beginning with capital letter designate values based upon The R.H.S. Colour Chart published by The Royal Horticultural society, London, England, 1995.

The following detailed description of the new variety is based upon observations taken of plants and fruits grown "underglass," i.e., under tunnel, in the farm of La Mogalla in Cartaya (Huelva), Spain, 7° W., 37° N., 45 feet elevation.

PROPAGATION

The new variety is principally propagated by way of root cuttings. Although propagation by root cuttings is presently preferred, other know methods of propagating raspberry plants may be used. Raspberries root and develop well after transplanting.

'Plapink 1004' is propagated by root cuttings. It is a primocane variety with fruit production from the end of September through the beginning of December on primocanes and in the ensuing year from the middle of February through the middle of May. 'Plapink 1004' is a self-fertile variety. It produces large quantities of pollen throughout the seasons and pollination is good.

Trials were pursued in in Cartaya (Huelva), Spain, about 7° W, 37° N, 45 feet elevation (15 meters high). The plants described are from high elevation nursery in Segovia, Spain, 3° 59'W., 41° 22'N., 2742 feet elevation. Plants were planted on June 14 in the first year and June 15 in the second year with a sample size of two repetitions every year and 120 plants per repetition every year. The growing period in Huelva, Spain, where the observations on primocane production were made, is between about June 15 and May 15 of the following year. 'Plapink 1004' is a primocane variety, with consistent fruit production beginning in the end of September and ending in the beginning of December on primocanes, and in the ensuing year from the middle of February through the middle of May. After planting as aforesaid, plants are grown in containers under tunnel. Water and fertilizer were applied through drip irrigation.

GENERAL

TABLE 1

Table 1 shows the accumulated production of 1st Quality Fruit (g/plant) of the new variety 'Plapink 1004' when compared to its closest varieties 'Adelita' (U.S. Plant Pat. No. 25,245) and 'Lupita' (U.S. Plant Pat. No. 25,171).

| Variety | End of September through beginning of December | Middle of February through middle of May | Total |
|---|---|---|---|
| Plapink 1004 | 1285.50 | 1109.10 | 2394.60 |
| ADELITA | 763.00 | 732.70 | 1495.70 |
| LUPITA | 253.10 | 201.00 | 454.10 |

TABLE 2

Table 2 shows the Accumulated Total Yield of 1st and 2nd quality fruit (g/plant) of the new variety 'Plapink 1004' when compared to its closest varieties 'Adelita' and 'Lupita'.

| Variety | 1st + 2nd Quality End of September through beginning of December | 1st + 2nd Quality Middle of February through middle of May | Total |
|---|---|---|---|
| Plapink 1004 | 1450.90 | 1227.90 | 2678.80 |
| ADELITA | 956.80 | 832.30 | 1789.10 |
| LUPITA | 559.50 | 431.10 | 990.50 |

TABLE 3

Table 3 shows the production from the end of September through the beginning of December of First Quality Fruit (1st quality) and Second Quality Fruit (2nd quality) in g/plant, of the new variety 'Plapink 1004' when compared to its closest varieties 'Adelita' and 'Lupita'.

| Variety | 1st Quality | 2nd Quality | TOTAL (1st Quality + 2nd Quality) | % 2nd Quality |
|---|---|---|---|---|
| Plapink 1004 | 1285.50 | 165.40 | 1450.90 | 11.40 |
| ADELITA | 763.40 | 193.40 | 956.80 | 20.21 |
| LUPITA | 253.10 | 306.40 | 559.50 | 54.76 |

% 2nd Quality = (2nd Quality/TOTAL) × 100

TABLE 4

Table 4 shows production from the middle of February through the middle of May of First Quality Fruit (1st quality) and Second Quality Fruit (2nd quality) in g/plant, of the new variety 'Plapink 1004' when compared to its closest varieties 'Adelita' and 'Lupita'.

| Variety | 1st Quality | 2nd Quality | TOTAL (1st Quality + 2nd Quality) | % 2nd Quality |
|---|---|---|---|---|
| Plapink 1004 | 1109.50 | 118.40 | 1227.90 | 9.64 |
| ADELITA | 732.70 | 99.60 | 832.30 | 11.97 |
| LUPITA | 201.00 | 230.10 | 431.10 | 53.37 |

% 2nd Quality = (2nd Quality/TOTAL) × 100

TABLE 5

Table 5 shows the weight (g/Fruit) in two production periods: September to December, and February to May of the new variety 'Plapink 1004' when compared to its closest varieties 'Adelita' and 'Lupita'.

| Variety | Middle October to end January | Middle April to end May |
|---|---|---|
| Plapink 1004 | 5.6-4.6 | 6.0-4.6 |
| ADELITA | 7.4-6.1 | 5.0-4.1 |
| LUPITA | 5.4-4.7 | 4.9-4.1 |

WEIGHT is shown as the average weight per fruit (g/fruit) in First Quality Fruits.

TABLE 6

Table 6 shows a comparison of the fruit analysis between the new variety 'Plapink 1004' and its closest varieties 'Adelita' and 'Lupita'.

FRUIT ANALYSIS

| | 'Plapink 1004' (10.09R.04) | 'Adelita' | 'Lupita' |
|---|---|---|---|
| Humidity & Volatile Matter (%) | 83.50 | 85.10 | 86.50 |
| Dry Matter (%) | 16.50 | 14.90 | 13.50 |
| pH (to 20°) | 2.80 | 3.00 | 2.90 |
| Acidity as Anhydride Citric (%) | 2.00 | 1.60 | 1.70 |
| Soluble Solids (° Brix) | 10.00 | 9.40 | 9.00 |
| Maturity Index | 5.00 | 5.90 | 5.30 |
| Content in Ascorbic Acid (ppm) | 246.90 | 193.00 | 293.10 |
| Dominant Tonality (nm) | 526 | 526 | 527 |
| Luminosity: Transmittance to 460 nm | 43.00 | 29.60 | 34.40 |

The following definitions apply:

Dry Matter refers to the residual weight left from the trituration of the fruit after the drying process at a temperature of 103° C.±2° C. until reaching constant weight. (%) Dry Matter=(Weight Dry Matter/Weight Fresh Matter)×100

Humidity & Volatile Matter represents the content in volatile matters and water of the fruits. (%) Humidity & Volatile Matter=100−% Dry Matter Maturity Index refers to the relation between Soluble solids and Acidity as Anhydride Citric.

Maturity Index=Soluble solids/Acidity as Anhydride Citric

Detailed description of the new variety: The following additional information is provided to further describe the new variety:

*Variety*.—'Plapink 1004'.

*Breeder ref.*—10.09R.04.

*Classification*.—*Rubus idaeus* L. Plants were grown in containers of 48 liters of capacity and are described during cultivar's primocane.

Plant:

*Growth habit*.—Semi-Upright.

*Vigor*.—Medium.

Cultivar's primocane cane:

*Length*.—About 160 cm to 200 cm.

*Diameter*.—About 1.0 cm to 1.4 cm.

*Texture*.—Smooth.

*Internode length*.—About 5.0 to 7.0 cm.

*Pubescence*.—Absent.

*Anthocyanin coloration of apex during rapid grow period*.—Weak.

*Cane color*.—RHS green group (near 143 C to 143 B).

Spines:

*Shape*.—Conical.

*Density*.—Medium.

*Number/cm*.—About 7 to 9.

*Length*.—About 0.1 cm to 0.15 cm.

*Width*.—About 0.08 cm to 0.12 cm at the base.

*Apex*.—Slightly curved.

*Color*.—RHS greyed red group color (near 178 B to 178 A).

*Texture*.—Rigid.

Leaf:

*Type*.—Compound.

*Number of leaflets*.—3.

*Arrangement of lateral leaflets*.—Touching.

*Overlapping of lateral leaflets with terminal leaflet*.—Absent.

*Upperside*.—RHS green group color (near 138 B to 138 A).

*Underside*.—RHS greyed-green group color (near 191 C to 191 B).

*Length*.—About 19.5 cm to 21.0 cm.

*Width*.—About 20.0 cm to 21.5 cm.

*Profile of leaflets in cross section*.—Concave.

*Relief between veins*.—Medium.

Lateral leaflet:

*Shape*.—Elliptic.

*Length*.—About 10.0 cm to 11.0 cm.

*Width*.—About 5.5 cm to 6.0 cm.

*Shape of tip*.—Acuminate.

*Shape of base*.—Obtuse.

*Shape of margin*.—Serrate.

*Upperside rugosity*.—Medium.

*Underside texture*.—Medium.

*Upperside coloration*.—RHS green group color (near 138 B to 138 A).

*Underside coloration*.—RHS greyed-green group color (near 191 C to 191 B).

*Venation pattern*.—Reticulate or penniveined.

*Upperside venation coloration*.—RHS greyed-yellow group color (near 147 D to 148 D).

*Underside venation coloration*.—RHS greyed-yellow group color (near 160 D to 160 C).

Terminal leaflet:
*Length/width ratio*.—Longer than broad.
*Length*.—About 11.0 cm to 11.5 cm.
*Width*.—About 9.0 cm to 9.5 cm.
*Cross section*.—Concave.
*Upperside*.—RHS green group color (near 138 B to 138 A).
*Underside*.—RHS greyed-green group color (near 191 C to 191 B).
*Shape of leaflet*.—Ovate.
*Shape of tip*.—Acuminate.
*Shape of base*.—Rounded.
*Shape of margin*.—Serrate.
*Upperside rugosity*.—Medium.
*Underside texture*.—Medium.
*Venation pattern*.—Reticulate or penniveined.
*Upperside venation coloration*.—RHS greyed-yellow green group color (near 147 D to 148 D).
*Underside venation coloration*.—RHS greyed-yellow green group color (near 160 D to 160 C).

Rachis:
*Length between the terminal leaflet and adjacent lateral leaflet*.—About 4.0 cm to 4.5 cm.
*Coloration*.—RHS yellow green group color (near 148 C to 148 D).

Petiole:
*Color*.—RHS yellow green group color (near 148 C to 148 D).
*Length*.—About 4.5 cm to 5.0 cm.
*Length* (*rachis with petiolule*).—About 8.5 cm to 9.5 cm.
*Diameter*.—About 3.5 mm to 4.0 mm in the Petiolule and about 2.0 mm to 2.5 mm in the rachis.
*Spines*.—Few.
*Petiole texture*.—Smooth.

Stipule:
*Quantity per leaf*.—2.
*Shape*.—Erect.
*Length*.—About 8.0 mm to 9.0 mm.
*Width*.—Very narrow. About 0.2 mm to 0.3 mm.
*Color* (*both surfaces*).—RHS yellow green group color (near 148 C to 148 D).

Flower bud:
*Shape*.—Trapezoidal.
*Diameter*.—About 7.0 mm to 8.5 mm.
*Length*.—About 9.5 mm to 10.0 mm.
*Color*.—RHS green group (near 138 D to 138 C).

Pedicel:
*Length*.—About 3.0 cm to 3.5 cm.
*Diameter*.—About 1.9 mm to 2.5 mm.
*Pedicel color*.—RHS green group color (near 143 D to 143 C).
*Surface texture*.—Smooth.
*Density of spines*.—Sparse.

Flower:
*Diameter*.—About 1.6 cm to 1.9 cm.
*Number of pistils per flower*.—About 105 to 130.
*Pistil length*.—About 3.5 mm to 4.0 mm
*Ovary shape*.—Pyriform.
*Ovary length*.—Medium.
*Ovary width*.—Narrow.
*Ovary color*.—RHS green group color (near 143 D to 143 C).
*Style length*.—About 0.10 cm to 0.15 cm.
*Style color*.—RHS yellow-green group color (near 145 D).
*Number of stamens per flower*.—About 115 to 140.
*Stamen length*.—About 0.3 cm to 0.4 cm.
*Stamen shape*.—Cylindrical lengthened.
*Stamen color*.—RHS green-white group color (near 157 D).
*Pollen amount*.—Moderate.
*Pollen color*.—RHS yellow green group color (near 153 C to 153 B).

Petal:
*Number of petals per flower*.—About 5.
*Shape*.—Narrow elliptique.
*Length*.—About 5.0 mm to 6.0 mm.
*Width*.—About 2.5 mm to 3.0 mm.
*Apex shape*.—Flat rounded.
*Base shape*.—Narrow.
*Margin*.—Smooth and regular.
*Texture*.—Smooth.
*Color* (*both surfaces*).—RHS white group color (near 155 B).

Peduncles:
*Length*.—about 16.0 cm to 18.0 cm.
*Diameter*.—about 4.0 mm to 4.5 mm.
*Surface texture*.—Smooth.
*Density of spines*.—Sparse to medium.
*Color*.—RHS green group (near 143 D to 143 C).

Receptacle:
*Length*.—About 1.2 cm to 1.4 cm.
*Diameter*.—About 0.8 cm to 1.0 cm.
*Shape*.—Conical.
*Color*.—RHS yellow-white group (near 158 C to 158 B).

Sepal:
*Number of sepals per flower*.—About 5.
*Shape*.—Triangular.
*Length*.—About 7.5 mm to 8.5 mm.
*Width*.—About 4.0 mm to 4.5 mm.
*Apex shape*.—Acuminate.
*Base shape*.—Large at the base forming the calyx.
*Margin*.—Smooth and regular.
*Texture*.—Smooth.
*Color*.—RHS green group color (near 145 C to 145 B).

Fruit:
*Shape*.—Conical.
*Length*.—About 2.4 cm to 2.6 cm.
*Width*.—About 2.3 cm to 2.5 cm.
*Color*.—RHS red group color (near 41 A to 42 A).
*Number of drupelets per fruit*.—About 100 to 115.
*Size of single drupelet*.—About 0.35 cm to 0.40 cm.
*Drupelet arrangement around the berry*.—Slightly irregular.
*Glossiness*.—Strong.
*Firmness*.—Medium.
*Adherence to plug*.—Medium.
*Diameter hollow center*.—About 0.9 cm to 1.0 cm.

Seed:
*Number of seeds per drupelet*.—1.
*Shape*.—Slightly reniform.
*Color*.—RHS greyed-orange group (near 165 C to 164 B).
*Surface texture*.—Wrinkled.

Fruiting lateral cane:
*Number of fruit per fruiting lateral cane*.—About 10 to 13 fruits.

*Average number of fruit per node.*—4 to 5 fruits.

Disease resistance: No particular sensitivity to any disease or pest has been observed for 'Plapink 1004'.

Use/market: The berries of 'Plapink 1004' are suitable for consumption as fresh fruit. Also, they are amenable to processing.

Fruit bearing type: Both on previous year's cane in autumn and current year's cane in spring.

Storage qualities: 'Plapink 1004' fruit maintain their quality characteristics when keeping them in a frigo chamber at temperatures of about 2° C. during 48 hours. The fruit's color remains substantially the same. Shelf life of 'Plapink 1004' is good.

Planting date: Each year about June 15 in the farm of La Mogalla, in Cartaya (Huelva), Spain, about 7° W, 37° N, 45 feet elevation.

Time of flowering: 10% Flowering on primocane occurs each year about August 9.

First mature fruits: Each year about September 23 (15-20 g/plant), with a maximum production at the beginning of November.

I claim:

1. A new and distinct raspberry plant of the variety substantially as shown and described.

* * * * *

10.09R.04